(12) United States Patent
Valint, Jr. et al.

(10) Patent No.: US 7,270,678 B2
(45) Date of Patent: *Sep. 18, 2007

(54) SURFACE MODIFICATION OF FUNCTIONAL GROUP-CONTAINING MEDICAL DEVICES WITH CATALYST-CONTAINING REACTIVE POLYMER SYSTEM

(75) Inventors: Paul L. Valint, Jr., Pittsford, NY (US); Joseph A. McGee, Dewitt, NY (US); Joseph C. Salamone, Boca Raton, FL (US)

(73) Assignee: Bausch & Lomb Incorporated, Rochester, NY (US)

( * ) Notice: Subject to any disclaimer, the term of this patent is extended or adjusted under 35 U.S.C. 154(b) by 91 days.

This patent is subject to a terminal disclaimer.

(21) Appl. No.: 10/187,154

(22) Filed: Jun. 28, 2002

(65) Prior Publication Data

US 2004/0006385 A1    Jan. 8, 2004

(51) Int. Cl.
*A61F 2/16*    (2006.01)
*A61F 2/14*    (2006.01)
(52) U.S. Cl. ...................... 623/6.62; 623/4.1
(58) Field of Classification Search ............... 623/4.1, 623/6.11, 6.16, 6.17, 6.56, 6.62
See application file for complete search history.

(56) References Cited

U.S. PATENT DOCUMENTS

| | | | |
|---|---|---|---|
| 3,996,187 A | 12/1976 | Travnicek | 260/37 |
| 3,996,189 A | 12/1976 | Travnicek | 260/37 |
| 4,418,165 A | 11/1983 | Polmanteer et al. | 523/210 |
| 4,647,282 A | 3/1987 | Fedorov et al. | 623/4 |
| 4,868,251 A | 9/1989 | Reich et al. | 525/479 |
| 5,326,506 A * | 7/1994 | Vanderbilt | 264/1.7 |
| 5,512,609 A | 4/1996 | Yang | 523/107 |
| 5,623,029 A | 4/1997 | Yang | 525/478 |
| 6,099,852 A * | 8/2000 | Jen | 424/429 |
| 6,180,687 B1 * | 1/2001 | Hammer et al. | 522/156 |
| 6,190,410 B1 * | 2/2001 | Lamielle et al. | 623/6.51 |
| 6,200,344 B1 * | 3/2001 | Lamielle et al. | 623/6.51 |
| 6,326,448 B1 | 12/2001 | Ojio et al. | 526/259 |
| 6,406,739 B1 | 6/2002 | LeBoeuf et al. | 427/2.24 |
| 6,428,839 B1 * | 8/2002 | Kunzler et al. | 427/2.1 |
| 6,440,571 B1 * | 8/2002 | Valint et al. | 428/447 |
| 6,599,559 B1 * | 7/2003 | McGee et al. | 427/2.24 |
| 6,630,243 B2 * | 10/2003 | Valint et al. | 428/420 |
| 6,638,563 B2 * | 10/2003 | McGee et al. | 427/2.24 |

FOREIGN PATENT DOCUMENTS

| | | |
|---|---|---|
| WO | WO 97/21497 | 6/1997 |
| WO | WO 00/72052 A1 | 11/2000 |

OTHER PUBLICATIONS

Polymeric Materials Science and Engineering, Washington DC vol. 76, Apr. 13, 1997 Surface-Active Macromonomers for Coating of Contact Lens Polymers 2 pages.

* cited by examiner

*Primary Examiner*—William H. Matthews

(57) ABSTRACT

Surface modified medical devices such as intraocular lens implants formed from one or more functional group-containing materials using reactive, hydrophilic polymers with catalyst functionality for the purpose of reducing or eliminating lens epithelial cell growth thereon, reducing or eliminating silicone oil absorption upon subsequent surgical exposure and/or reducing implantation inserter friction is provided herein. Additionally, a method of making and using surface modified intraocular lens implants is provided.

15 Claims, No Drawings

SURFACE MODIFICATION OF FUNCTIONAL GROUP-CONTAINING MEDICAL DEVICES WITH CATALYST-CONTAINING REACTIVE POLYMER SYSTEM

FIELD OF THE INVENTION

The present invention relates generally to surface modification of functional group-containing polymeric materials used in the manufacture of medical devices. More specifically, the present invention relates to surface modification of intraocular lens implants formed from one or more functional group-containing materials using reactive, hydrophilic polymers having catalyst function for the purpose of reducing or eliminating lens epithelial cell growth thereon.

BACKGROUND OF THE INVENTION

Since the 1940's ophthalmic medical devices in the form of intraocular lens (IOL) implants have been utilized as replacements for diseased or damaged natural ocular lenses. In most cases, an IOL is implanted within an eye at the time of surgically removing the diseased or damaged natural lens, such as for example, in the case of cataracts. For decades, the preferred material for fabricating such IOL implants was poly(methyl methacrylate) (PMMA), which is a rigid, glassy polymer.

Softer, more flexible IOL implants have gained in popularity in more recent years due to their ability to be compressed, folded, rolled or otherwise deformed. Such softer IOL implants may be deformed prior to insertion thereof through an incision in the cornea of an eye. Following insertion of the IOL in an eye, the IOL returns to its original pre-deformed shape due to the memory characteristics of the soft material. Softer, more flexible IOL implants as just described may be implanted into an eye through an incision that is much smaller, i.e., less than 4.0 mm, than that necessary for more rigid IOLs, i.e., 5.5 to 7.0 mm. A larger incision is necessary for more rigid IOL implants because the lens must be inserted through an incision in the cornea slightly larger than the diameter of the inflexible IOL optic portion. Accordingly, more rigid IOL implants have become less popular in the market since larger incisions have been found to be associated with an increased incidence of postoperative complications, such as induced astigmatism.

With recent advances in small-incision cataract surgery, increased emphasis has been placed on developing soft, foldable materials suitable for use in the manufacture of IOL implants. In general, the materials of current commercial IOLs fall into one of three categories: silicone, hydrophilic acrylic and hydrophobic acrylic.

In general, IOLs, once implanted, have a tendency to allow lens epithelial cells (LECs) to attach and spread on the surface of the IOL. Such LEC growth on IOL surfaces causes undesirable IOL opacification requiring IOL explantation and replacement. Also undesirable, IOLs manufactured from silicone materials tend to absorb silicone oils used in subsequent unrelated ocular surgeries causing opacification of the IOL.

Because of the noted shortcomings of current biocompatible polymeric materials available for use in the manufacture of ophthalmic devices such as IOLs, there is a need for stable, biocompatible polymeric materials suitable for use in the manufacture of IOLs that reduce or eliminate LEC growth on surfaces thereof upon implantation and reduce or eliminate the risk of IOL absorption of silicone oil in the case of subsequent ocular surgeries.

SUMMARY OF THE INVENTION

Surface modification of functional group-containing polymeric materials useful in the manufacture of contact lenses and medical device implants such as intraocular lenses (IOLs) in accordance with the present invention utilizes reactive, hydrophilic polymers having catalyst function. Reactive, hydrophilic polymers having catalyst function are used to accelerate the formation of covalent chemical linkages with the surface of contact lenses and IOLs or like implants manufactured from functional group-containing polymeric materials. Such acceleration of covalent chemical linkages simplifies the coating process and reduces associated costs. The preferred reactive, hydrophilic polymers having catalyst function of the present invention are selected based on the specific functional group-containing polymeric material to be coated. In accordance with the present invention, the one or more reactive, hydrophilic polymers having catalyst function selected for surface modification must have complementary chemical functionality to that of the one or more functional group-containing polymeric materials to be coated. Such complementary chemical functionality enables a chemical reaction between the functional groups of the polymeric material and the reactive, hydrophilic polymer to form covalent chemical linkages therebetween. The catalyst function of the reactive, hydrophilic polymer accelerates the formation of covalent chemical linkages therebetween. The one or more reactive, hydrophilic polymers are thus chemically bound to the surface of the one or more functional group-containing polymeric materials of the contact lens, IOL or like medical device to achieve surface modification thereof. Such surface modification of an IOL implant reduces or eliminates silicone oil absorption upon subsequent exposure, reduces or eliminates surface calcification, reduces or eliminates lens epithelial cell surface growth and/or reduces friction upon passage through an inserter for implantation.

Accordingly, it is an object of the present invention to provide a surface modifying coating for biocompatible polymeric compositions having desirable physical characteristics for use in the manufacture of ophthalmic devices.

Another object of the present invention is to provide a surface modifying coating for polymeric compositions having a relatively high refractive index.

Another object of the present invention is to provide a surface modifying coating for polymeric compositions suitable for use in the manufacture of an ophthalmic implant.

Another object of the present invention is to provide a surface modifying coating for polymeric compositions that reduces or eliminates lens epithelial cell surface growth following implantation thereof in an eye.

Another object of the present invention is to provide a surface modifying coating for polymeric compositions that reduces or eliminates surface calcification following implantation thereof in an eye.

Another object of the present invention is to provide a surface modifying coating for surgical implants that reduces friction by the coated implant when passed through an implantation inserter.

Still another object of the present invention is to provide a surface modifying coating for polymeric compositions that is relatively simple to produce and use.

These and other objectives and advantages of the present invention, some of which are specifically described and others that are not, will become apparent from the detailed description and claims that follow.

DETAILED DESCRIPTION OF THE INVENTION

Surface structure and composition determine many of the physical properties and ultimate uses of solid materials. Characteristics such as wetting, friction, electrostatic charging and adhesion are largely influenced by surface characteristics. Of particular concern are the effects of such surface characteristics on biocompatibility. The alteration of surface characteristics is therefore of special significance in biotechnical applications such as in the case of medical devices such as implants.

The following detailed description is provided to enable any person skilled in the art to which the present invention pertains to make and use the same, and sets forth the best mode contemplated by the inventors of carrying out the subject invention.

The present invention relates to surface modification of medical devices such as but not limited to intraocular lenses (IOLs) through the use of complementary reactive functionality. Although only IOLs will be referred to hereinafter for purposes of simplicity, such reference is not intended to be limiting since the subject method is suitable for surface modification of other medical devices and implants, as well as IOLs. For surface modification of IOLs in accordance with the present invention, complementary reactive functionality is incorporated between the IOL material and the surface modification treatment polymer (SMTP). For example, if a reactive hydrophilic SMTP has epoxide functionality, then the IOL material to be treated must have a complementary functionality that will react with that of the SMTP. In such a case, the IOL material could include an alcohol-based monomer such as 2-hydroxyethyl methacrylate to react with the SMTP epoxide functionality. Likewise, if an IOL is formed from an epoxide monomer-containing material, a hydrophilic SMTP containing a 2-hydroxyethyl methacrylate copolymer could be used for surface modification in accordance with the present invention.

The surface modification method of the present invention preferably uses one or more reactive, SMTPs along with a chemical additive to coat IOLs. The chemical additive serves to impart a catalyst function within at least one of the reactive, SMTPs to accelerate the coating process. The reactive, SMTPs of the present invention are copolymers of various hydrophilic monomers with at least one monomer having reactive chemical functionality complementary to the chemical functionality of the IOL to be coated. For example, an IOL to be coated in accordance with the present invention contains carboxylic acid functional groups. So as to achieve complementary chemical functionality, one of the copolymers forming the SMTP may contain glycidyl methacrylate (GMA) monomer units and N,N-dimethylacrylamide (DMA) monomer units. The SMTP may likewise include a hydrophilic terpolymer containing carboxylic acid functional groups and a third monomer or chemical additive which can be, for example, 3-(N,N-dimethylamino)propyl methacrylamide, (DMAPMA). In this SMTP system, DMAPMA serves as a tertiary amine catalyst.

Suitable hydrophilic monomers for use in accordance with the present invention can be aprotic types such as acrylamides and N-vinylpyrrolidone, or protic types such as methacrylic acid and 2-hydroxyethyl methacrylate. Specific examples of suitable hydrophilic monomers include but are not limited to N,N-dimethylacrylamide, N,N-dimethylmethacrylamide, N-methylmethacrylamide and N-methylacrylamide but preferably N,N-dimethylacrylamide for increased hydrophilicity.

Suitable monomers having reactive chemical functionality include for example but are not limited to monomers having epoxide, carboxylic acid, anhydride, oxazolinone and alcohol functionalities.

Suitable chemical additives to impart catalyst function to the reactive, SMTPs include but are not limited to 3-(N,N-dimethylamino)propyl methacrylamide, 2-(N,N-dimethylamino)ethyl methacrylate, 2-(N,N-dimethylamino)ethyl acrylate, (N,N-dimethyl aminomethyl)styrene, N-[3-(N,N-dimethylamino)propyl]acrylamide and 3-(N,N-dimethylamino)propyl acrylate.

Examples of suitable reactive SMTPs having catalyst function include but are not limited to copolymers and terpolymers of the above described hydrophilic monomers with at least one monomer having reactive chemical functionality and at least one monomer or chemical additive having catalyst functionality. Such reactive, SMTPs are produced through free radical polymerization techniques known to those skilled in the art.

Suitable functional group-containing polymeric materials useful in the manufacture of medical devices such as contact lenses, IOLs, corneal inlays, corneal onlays, and the like in accordance with the present invention have clarity, a relatively high refractive index of approximately 1.40 or greater, a relatively low glass transition temperature of approximately 25° Celsius or less, and a relatively high elongation of approximately 80 percent or greater. Such functional group-containing polymeric materials of the present invention, possessing the particular physical characteristics described, likewise possess functional groups such as for example but not limited to hydroxy functional groups, carboxylic acid functional groups, oxazolone functional groups, anhydride functional groups, acid chloride functional groups, reactive ester functional groups and epoxide functional groups. Examples of suitable polymeric materials having hydroxy functional groups include but are not limited to 2-hydroxyethyl methacrylate, glyceryl methacrylate and 2-hydroxypropyl methacrylamide. Examples of suitable polymeric materials having carboxylic acid functional groups include but are not limited to methacrylic acid, acrylic acid and N-carboxy-β-alanine-N-vinyl ester. Examples of suitable polymeric materials having oxazolone functional groups include but are not limited to 2-isopropenyl-4,4-dimethyl-2-oxazolin-5-one, 2-vinyl-4,4-dimethyl-2-oxazolin-5-one, spiro-4'-(2'-isopropenyl-2'-oxazolin-5-one) cyclohexane, spiro-4'-(2'-vinyl-2'-oxazolin-5'-one) cyclohexane and 2-(1 -propenyl)-4,4-dimethyl-oxazolin-5-one. Examples of suitable polymeric materials having anhydride functional groups include but are not limited to methacrylic anhydride, maleic anhydride and acrylic anhydride. An example of a suitable polymeric material having epoxide functional groups includes but is not limited to glycidyl methacrylate.

Suitable functional group-containing polymeric materials for the production of an IOL or like medical device of the present invention include but are not limited to foldable or compressible materials, such as silicone polymers, hydrocarbon and fluorocarbon polymers, hydrogels, soft acrylic polymers, polyesters, polyamides, polyurethane, silicone polymers with hydrophilic monomer units, fluorine-containing polysiloxane elastomers and combinations thereof. One preferred functional group-containing polymeric material of the present invention is a hydrogel made from 2-hydroxyethyl methacrylate (HEMA) and 6-hydroxyhexyl methacrylate (HOHEXMA), i.e., poly(HEMA-co-HOHEXMA). Poly (HEMA-co-HOHEXMA) is a preferred polymeric material for the manufacture of IOL implants due to its equilibrium water content of approximately 18 percent by weight, and high refractive index of approximately 1.474, which is greater than that of the aqueous humor of the eye, i.e., 1.336.

A high refractive index is a desirable feature in the production of IOLs to impart high optical power with a minimum of optic thickness. By using a material with a high refractive index, visual acuity deficiencies may be corrected using a thinner IOL. Poly(HEMA-co-HOHEXMA) is a desirable material in the production of IOL implants due to its mechanical strength, which is suitable to withstand considerable physical manipulation. Poly(HEMA-co-HOHEXMA) also has desirable recovery properties suitable for IOL implant use. IOL implants manufactured from a material possessing desirable recovery properties such as poly(HEMA-co-HOHEXMA) unfold in a more controlled manner in an eye, rather than explosively, to its predetermined shape. Explosive unfolding of IOL implants is undesirable due to potential damage to delicate tissues within the eye. Poly(HEMA-co-HOHEXMA) also has dimensional stability in the eye, which is likewise desirable.

Although the teachings of the present invention are preferably applied to soft or foldable IOL implants or like medical devices formed of a foldable or compressible material, the same may also be applied to harder, less flexible lenses formed of a relatively rigid material such as poly(methyl methacrylate) (PMMA) having flexible haptics formed either of the same or a different material.

In accordance with the present invention, the one or more functional group-containing polymeric materials are used to produce an IOL implant containing functional groups. One or more reactive, hydrophilic SMTPs of the present invention having catalyst functionality as described above, are then selected so as to have chemical functionality complementary to that of the one or more functional group-containing polymeric materials comprising the IOL. Such complementary chemical functionality enables a chemical reaction to occur between the functional groups at the surface of the polymeric material forming the IOL and the functional groups of the one or more reactive, hydrophilic SMTPs. This chemical reaction between functional groups forms covalent chemical linkages therebetween. The catalyst functionality of the reactive, hydrophilic SMTPs serves to accelerate the chemical reaction between functional groups to shorten the time required for the surface modification process. According to the surface modification process of the present invention, an IOL polymeric material having hydroxy functional groups would preferably undergo surface modification using reactive, hydrophilic SMTPs containing carboxylic acid functional groups, isocyanate functional groups or epoxy functional groups. Likewise, an IOL polymeric material having carboxylic acid groups would preferably undergo surface modification using reactive, hydrophilic SMTPs containing glycidyl methacrylate (GMA) monomer units to provide epoxy functional groups.

Surface modification of IOLs produced from one or more functional group-containing polymeric materials using one or more reactive, hydrophilic SMTPs having catalyst functionality in accordance with the present invention is described in still greater detail in the examples that follow.

EXAMPLE 1

Synthesis of Reactive, Hydrophilic Copolymer of N,N-dimethylacrylamide (DMA) and Glycidyl Methacrylate (GMA)

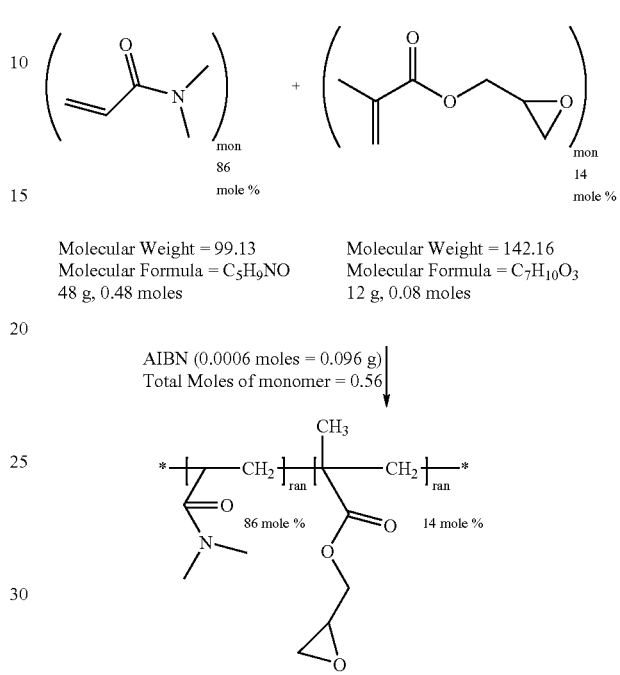

To a one liter reaction flask were added distilled N,N-dimethylacrylamide (DMA, 48 gm, 0.48 moles), distilled glycidyl methacrylate (GMA, 12 gm, 0.08 moles), 2,2'-azobisisobutyronitrile (AIBN, 0.096 gm, 0.0006 moles) and toluene (600 ml). The reaction vessel was fitted with a magnetic stirrer, condenser, thermal controller and a nitrogen inlet. Nitrogen was bubbled through the solution for 15 minutes to remove any dissolved oxygen. The reaction flask was then heated to 60° Celsius under a passive blanket of nitrogen for twenty hours. The reaction mixture was then added slowly to six liters of ethyl ether with good mechanical stirring. The reactive polymer precipitated and was collected by vacuum filtration. The solid was placed in a vacuum oven at 30° Celsius overnight to remove the ether leaving 50.1 gm of reactive polymer (an 83 percent yield). The reactive polymer was placed in a desiccator for storage until use.

The general procedure of example one was followed to prepare the reactive SMTPs (Examples 1b-1e) listed in Table 1 below.

TABLE 1

Examples 1b-1e: Reactive DMA-co-GMA Polymers

| Example | DMA grams | DMA moles | DMA x mole % | GMA grams | GMA moles | GMA y mole % | AIBN moles | Solvent | volume ml | Time (hours) | Yield grams |
|---|---|---|---|---|---|---|---|---|---|---|---|
| 1b | 57 | 0.58 | 97 | 3 | 0.02 | 3 | 0.0006 | toluene | 600 | 20 | 50.4 |
| 1c | 54 | 0.54 | 93 | 6 | 0.042 | 7 | 0.0006 | toluene | 600 | 20 | 53.5 |
| 1d | 42 | 0.42 | 76 | 18 | 0.13 | 24 | 0.0006 | toluene | 600 | 20 | 46.7 |
| 1e | 36 | 0.36 | 68 | 24 | 0.17 | 32 | 0.0006 | toluene | 600 | 20 | 49.8 |

EXAMPLE 2

Synthesis of a Water Soluble Reactive Polymer of N,N-dimethylacrylamide (DMA), 1H,1H,5H-octafluoropentyl Methacrylate (OFPMA) and Glycidyl Methacrylate (GMA)

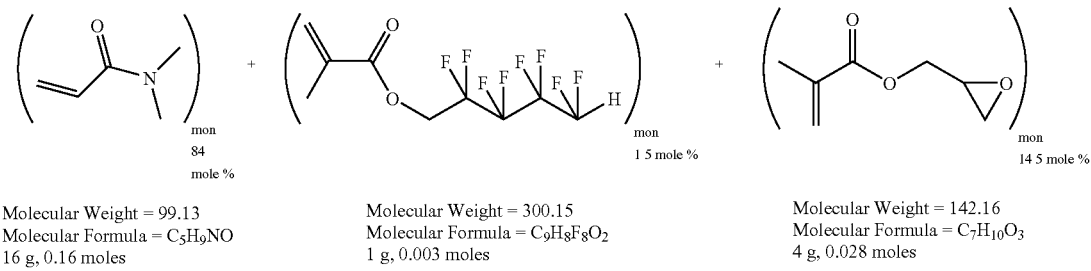

Molecular Weight = 99.13
Molecular Formula = C5H9NO
16 g, 0.16 moles

Molecular Weight = 300.15
Molecular Formula = C9H8F8O2
1 g, 0.003 moles

Molecular Weight = 142.16
Molecular Formula = C7H10O3
4 g, 0.028 moles

AIBN (0.00018 moles = 0.03 g)
Total Moles of monomer = 0.191

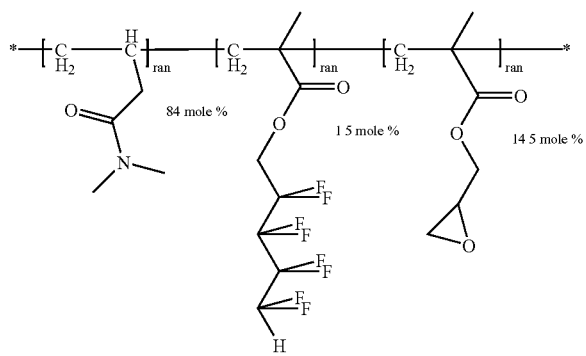

To a 500 ml reaction flask were added distilled N,N-dimethylacrylamide (DMA, 16 gm, 0.16 moles), 1H,1H,5H-octafluoropentyl methacrylate (OFPMA, 1 gm, 0.003 moles, used as received), distilled glycidyl methacrylate (GMA, 4 gm, 0.028 moles), 2,2'-azobisisobutyronitrile (AIBN, 0.03 gm, 0.00018 moles) and toluene (300 ml). The reaction vessel was fitted with a magnetic stirrer, condenser, thermal controller and a nitrogen inlet. Nitrogen was bubbled through the solution for 15 minutes to remove any dissolved oxygen. The reaction flask was then heated to 60° Celsius under a passive blanket of nitrogen for twenty hours. The reaction mixture was then added slowly to 3 liters of ethyl ether with good mechanical stirring. The reactive polymer precipitated and was collected by vacuum filtration. The solid was placed in a vacuum oven at 30° Celsius overnight to remove the ether leaving 19.3 gm of reactive polymer (92 percent yield). The reactive polymer was placed in a desiccator for storage until use.

The general procedure of Example 2 was followed to prepare the reactive SMTPs (Examples 2b-2e) listed in Table 2 below. Reaction times for all the syntheses given in Table 2 were 20 hours and the solvent was tetrahydrofuran (600 ml). The AIBN levels for all the reactions given in Table 2 were 0.0006 moles.

TABLE 2

Examples 2b-2e: Reactive DMA-co-OFPMA-co-GMA Polymers

| Example | DMA grams | DMA moles | DMA x mole % | OFPMA grams | OFPMA moles | OFPMA y mole % | GMA grams | GMA moles | GMA z mole % | Yield grams |
|---|---|---|---|---|---|---|---|---|---|---|
| 2b | 51.4 | 0.52 | 91 | 2.6 | 0.0087 | 1.5 | 6 | 0.042 | 7.4 | 47.6 |
| 2c | 39.5 | 0.4 | 74.3 | 2.5 | 0.0083 | 1.5 | 18 | 0.13 | 24.2 | 50.2 |

TABLE 2-continued

Examples 2b-2e: Reactive DMA-co-OFPMA-co-GMA Polymers

| Example | DMA grams | DMA moles | DMA x mole % | OFPMA grams | OFPMA moles | OFPMA y mole % | GMA grams | GMA moles | GMA z mole % | Yield grams |
|---|---|---|---|---|---|---|---|---|---|---|
| 2d | 33.6 | 0.34 | 65.7 | 2.4 | 0.008 | 1.5 | 24 | 0.17 | 32.8 | 48.8 |
| 2e | 54.4 | 0.55 | 95 | 2.65 | 0.0088 | 1.5 | 3 | 0.02 | 3.5 | 40.2 |

EXAMPLE 2f

Synthesis of Reactive, Hydrophilic Copolymer of N,N-dimethylacrylamide (DMA), 1H,1H,5H-octafluoropentyl Methacrylate (OFPMA), Glycidyl Methacrylate (GMA) and Polyethylene Glycol 1000 Monomethylether Methacrylate (PEGMA)

To a 500 ml reaction flask were added distilled N,N-dimethylacrylamide (DMA, 8 g, 0.08 moles), 1H,1H,5H-octafluoropentyl methacrylate (OFPMA, 1 g, 0.003 moles, used as received), distilled glycidyl methacrylate (GM, 4 g, 0.028 moles) polyethylene glycol 1000 monomethyl ether methacrylate (PEGMA, 8 g, 0.007 moles), 2,2'-azobisisobutyronitrile (AIBN, 0.03 g, 0.00018 moles) and tetrahydrofuran (THF, 300 ml). The reaction vessel was fitted with a magnetic stirrer, condenser, thermal controller and a nitro-

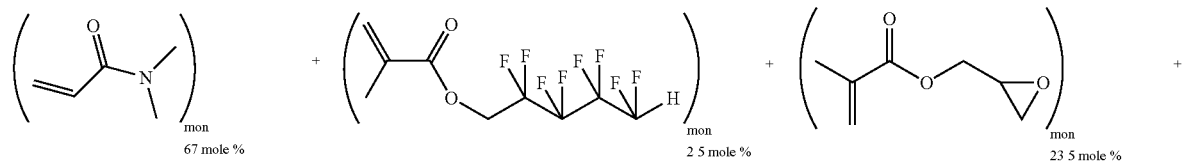

Molecular Weight = 99.13
Molecular Formula = $C_5H_9NO$

Molecular Weight = 300.15
Molecular Formula = $C_9H_8F_8O_2$

Molecular Weight = 142.16
Molecular Formula = $C_7H_{10}O_3$

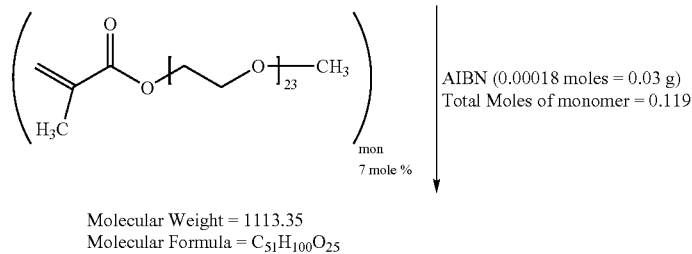

AIBN (0.00018 moles = 0.03 g)
Total Moles of monomer = 0.119

Molecular Weight = 1113.35
Molecular Formula = $C_{51}H_{100}O_{25}$

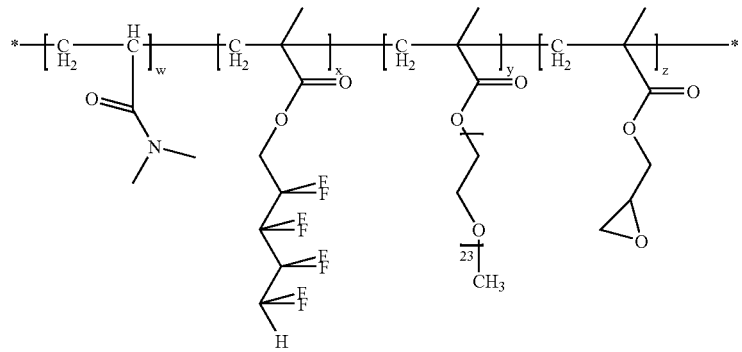

gen inlet. Nitrogen was bubbled through the solution for 15 minutes to remove any dissolved oxygen. The reaction flask was then heated to 60° C. under a passive blanket of nitrogen for 72 hours. Flash evaporation of the solvent followed by freeze drying left 8.8 g of reactive polymer (42% yield), a wax like semi-solid.

EXAMPLE 2g

Synthesis of Reactive, Hydrophilic Copolymer of N-Vinyl-2-pyrrolidinone (NVP) and 4-Vinylcyclohexyl-1,2-epoxide (VCHE)

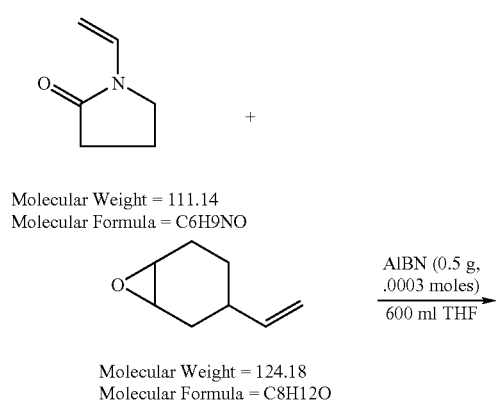

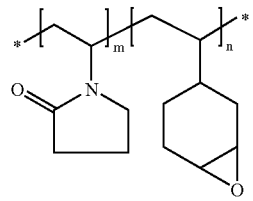

To a 1L reaction flask were added distilled N-vinyl-2-pyrrolidinone (NVP, 53.79 g, 0.48 moles), 4-vinylcyclohexyl-1,2-epoxide (VCHE, 10.43 g, 0.084 moles), 2,2'-azobisisobutyronitrile (AIBN, 0.05 g, 0.0003 moles) and tetrahydrofuran (THF, 600 ml). The reaction vessel was fitted with a magnetic stirrer, condenser, thermal controller and a nitrogen inlet. Nitrogen was bubbled through the solution for 15 minutes to remove any dissolved oxygen. The reaction flask was then heated to 60° C. under a passive blanket of nitrogen for 20 hours. The reaction mixture was then added slowly to 6 L of ethyl ether with good mechanical stirring. The copolymer precipitated and was collected by vacuum filtration. The solid was placed in a vacuum oven at 30° C. overnight to remove the ether leaving 21 g of reactive polymer (a 32% yield). The reactive polymer was placed in a desiccator for storage until use.

EXAMPLE 3

Synthesis of a Reactive Polymer Containing Tertiary Amine Groups

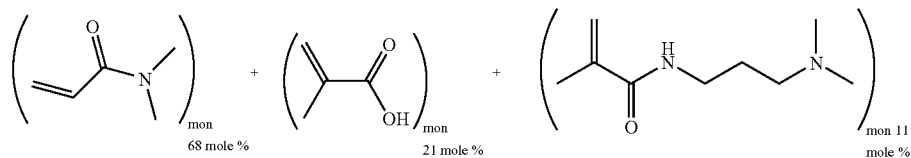

AIBN (0.0002 moles = 0.0328 g) | THF (50 ml)
Total Moles of monomer = 0.235 | Water (50 ml)

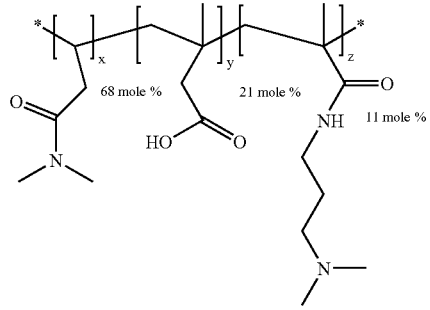

Reagents N,N-dimethylacrylamide (DMA, 16 gm, 0.16 moles), methacrylic acid (MAA, 4 gm, 0.05 moles) and 3-(N,N-dimethylamino)propyl methacrylamide (DMAPMA, 4.34 gm, 0.025 moles) were combined in a 1:1 mixture of tetrahydrofuran (THF, 50 ml) and purified water (50 ml). Oxygen was removed from the system with a fifteen minute bubbling stream of nitrogen. AIBN (0.0328 gm, 0.0002 moles) was added and the temperature was raised to 60° Celsius under a passive blanket of nitrogen for twenty-four hours. Solvents were removed by flash evaporation. The polymer was then dissolved in 200 ml of 2-propanol, and dried over $MgSO_4$. The reactive polymer was isolated by precipitation from a large volume of ethyl ether (2 liters). The polymer was then dried under house vacuum for twenty-four hours (11 gram yield).

EXAMPLE 4

Synthesis of a Reactive Polymer Containing Tertiary Amine Groups

To a 1000 ml reaction flask were added N,N-dimethylacrylamide (DMA, 32 gm, 0.32 moles), methacrylic acid (MAA, 4 gm, 0.05 moles), 3-(N,N-dimethylamino)propyl methacrylamide (DMAPMA, 17.36 gm, 0.102 moles, used as received), AIBN (0.0656 gm, 0.00004 moles), tetrahydrofuran (THF, 200 ml) and distilled water (200 mL). The reaction vessel was fitted with a magnetic stirrer, condenser, thermal controller and a gas inlet. Nitrogen was bubbled through the solution to remove any dissolved oxygen. The reaction flask was then heated to 60° Celsius for twenty-four hours. The polymer was then dissolved in three liters of methanol, and dried over $MgSO_4$. The reactive polymer was isolated by precipitation from a large volume of ethyl ether (8 liters). The polymer was then dried under house vacuum for twenty-four hours at 30° Celsius. Polymer yield was 32.78 gm (61.43 percent). The reactive polymer was placed in a desiccator for storage until use.

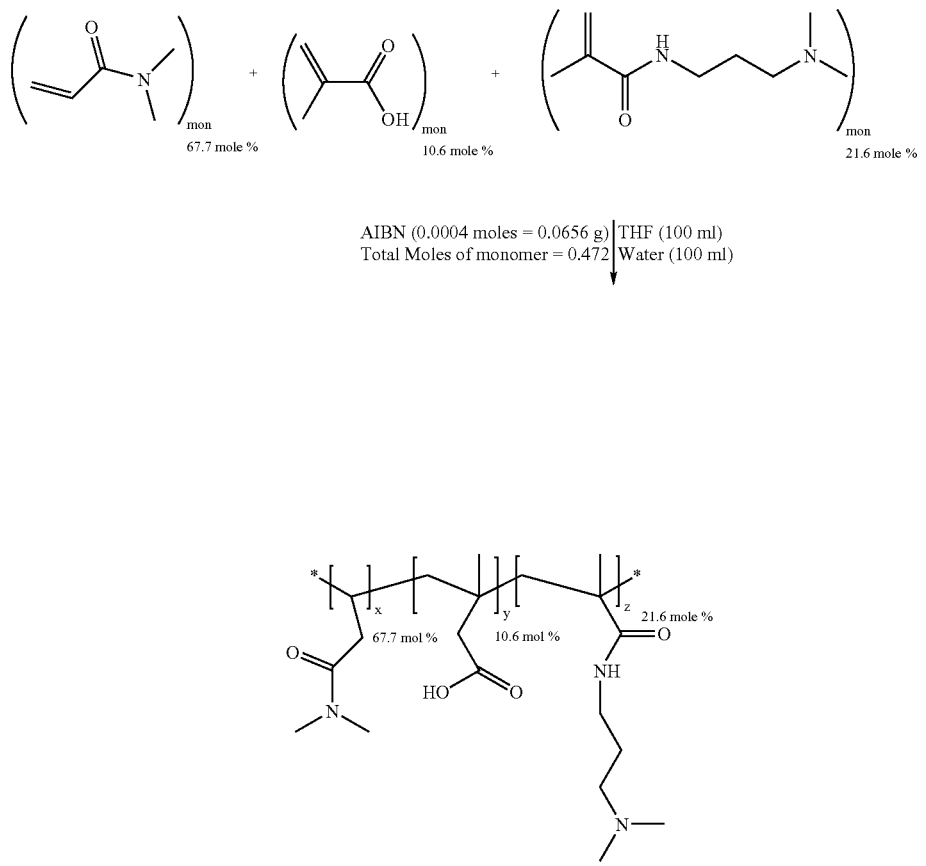

EXAMPLE 5

Synthesis of a Reactive Polymer DMA-co-MAA

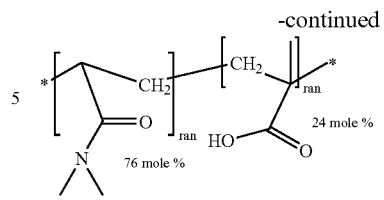

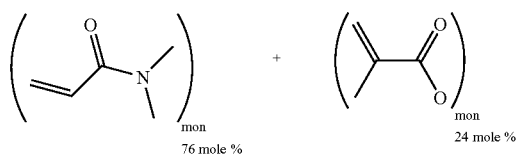

Molecular Weight = [99.13] mon
Molecular Formula = [$C_5H_9NO$] mon
128 g, 1.28 moles Molecular Weight = [86.09] mon
Molecular Formula = [$C_4H_6O_2$] mon
32 g, 0.37 moles AIBN (0.0016 moles = 0.24 g)
Total Moles of monomer = 1.56
Anhydrous 2-propanol 2000 ml To a 3000 ml reaction flask were added distilled DMA (128 gm, 1.28 moles), MAA (32 gm, 0.37 moles), AIBN (0.24 gm, 0.0016 moles) and anhydrous 2-propanol (2000 ml). The reaction vessel was fitted with a magnetic stirrer, condenser, thermal controller and a nitrogen inlet. Nitrogen was bubbled through the solution for fifteen minutes to remove any dissolved oxygen. The reaction flask was then heated to 60° Celsius under a passive blanket of nitrogen for seventy-two hours. The volume of the reaction mixture was reduced by half by flash evaporation. The reactive polymer was precipitated into eight liters of ethyl ether and then collected by vacuum filtration. The solid was placed in a vacuum oven at 30° Celsius overnight to remove the ether leaving 142.34 gm of reactive polymer (89 percent yield). The reactive polymer was placed in a desiccator for storage until use.

The general procedure of Example 5 was followed to prepare the reactive SMTPs (Examples 5b-5c) listed in Table 3 below.

TABLE 3

Examples 5b-5c: Reactive DMA-co-MAA Polymers

| Example | DMA grams | DMA moles | DMA x mole % | MAA grams | MAA moles | MAA y mole % | AIBN moles | Solvent | vol. ml | Time (hours) | Yield grams |
|---|---|---|---|---|---|---|---|---|---|---|---|
| 5b | 42 | 0.42 | 67 | 18 | 0.21 | 33 | 0.0006 | 2-propanol | 750 | 72 | 49.63 |
| 5c | 36 | 0.36 | 56 | 24 | 0.28 | 44 | 0.0006 | 2-propanol | 750 | 72 | 44.97 |

EXAMPLE 6

Medical Device Surface Modification

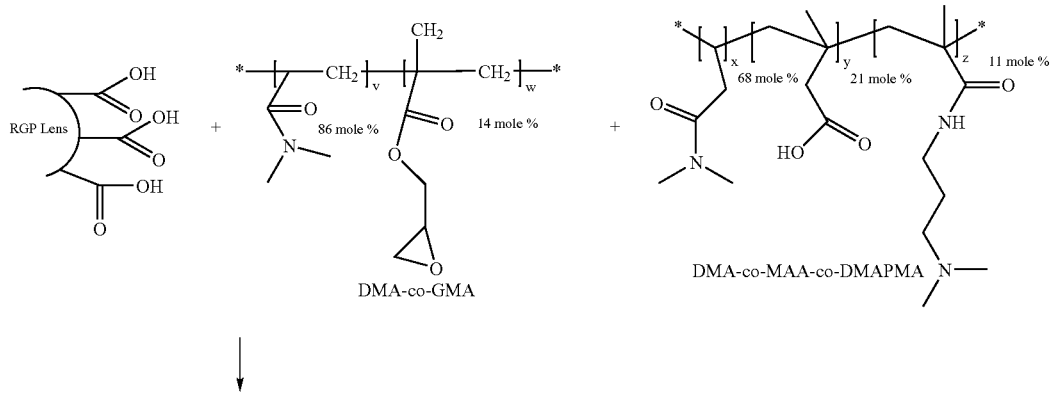

-continued

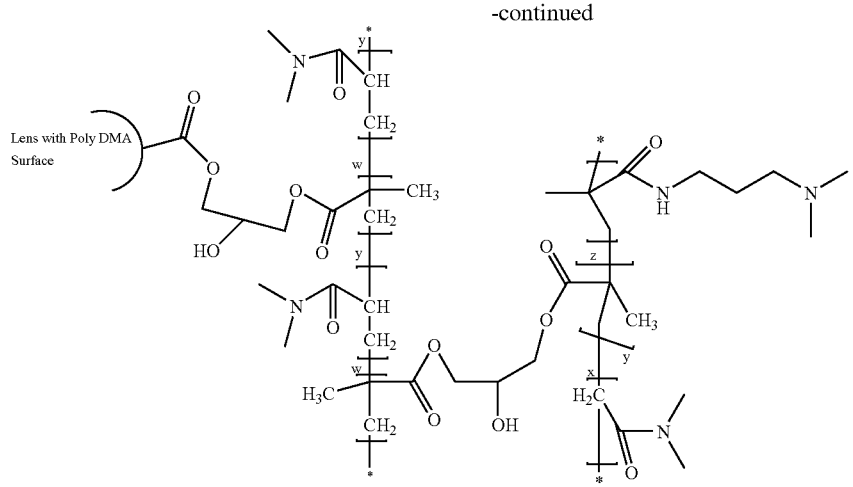

Boston XO™ (Bausch & Lomb Incorporated, Rochester, N.Y.) lenses were first cleaned with Boston Advance™ (Bausch & Lomb Incorporated, Rochester, N.Y.) cleaning solution. Solutions of reactive polymers DMA-co-GMA from Example 1 and DMA-co-MA-co-DMAPMA from Example 3 were prepared as follows. The first was a solution of DMA-co-GMA [86/14] (4.0 gm/80 ml of water). The second solution was prepared with DMA-co-MA-co-DMAPMA [68/21/11] (4.0 gm/80 ml of water). The polymer solutions were passed through Millipore™ 5-micron type LS (Millipore Products, Bedford, Mass.) membrane filters and then combined to give a mixed solution of 5 percent polymer by weight. Lenses were then placed in the 5 ml of reactive polymer mixture and allowed to stand for four, eight and sixteen hours at room temperature or at 55° Celsius for one hour. The treated lenses were then rinsed off twice with purified water, padded dry with Kim Wipe™ (Kimberly-Clark, Inc., Mississauga, Ontario) tissue and submitted for x-ray photoelectron spectroscopy (XPS) analysis the results of which are set forth below in Table 4. Clearly the lenses are coated with the nitrogen-containing polymers. The nitrogen level increases from 0.1 (=0) to >3 percent while the fluorine and silicone levels drop. The fluorine ratio was calculated as follows: $[F]_{control} - [F]_{test}/[F]_{control}$. The value represents the amount of fluorine covered up by the coating polymer where 1=100 percent covered.

TABLE 4

XPS Results from Example 6

|  | C1s | N1s | O1s | F1s | Si2p | [F] Ratio |
|---|---|---|---|---|---|---|
| Controls |  |  |  |  |  |  |
| Average | 54.88 | 0.10 | 19.25 | 19.78 | 5.99 | 0.00 |
| Std. Dev. | 0.5 | 0.1 | 0.2 | 0.8 | 0.4 |  |
| Controls Cleaned |  |  |  |  |  |  |
| Average | 56.22 | 0.13 | 19.92 | 17.93 | 5.42 | 0.00 |
| Std. Dev. | 1.7 | 0.3 | 2.4 | 4.4 | 0.2 |  |
| P-C RGP 4 HR. at Room Temp. |  |  |  |  |  |  |
| Average | 58.65 | 2.34 | 20.26 | 13.48 | 5.28 | 0.25 |
| Std. Dev. | 0.6 | 0.4 | 0.4 | 0.6 | 0.6 |  |
| P-C RGP 8 HR. at Room Temp. |  |  |  |  |  |  |
| Average | 60.77 | 3.40 | 19.50 | 11.91 | 4.42 | 0.34 |
| Std. Dev. | 0.4 | 0.4 | 0.2 | 1.0 | 0.2 |  |

TABLE 4-continued

XPS Results from Example 6

|  | C1s | N1s | O1s | F1s | Si2p | [F] Ratio |
|---|---|---|---|---|---|---|
| P-C RGP 16 HR. at Room Temp. |  |  |  |  |  |  |
| Average | 60.37 | 3.42 | 19.25 | 12.15 | 4.81 | 0.32 |
| Std. 0ev. | 0.9 | 0.8 | 0.8 | 1.6 | 0.9 |  |
| P-C RGP at 55° C. for 1 HR. |  |  |  |  |  |  |
| Average | 61.35 | 3.84 | 19.34 | 11.38 | 4.09 | 0.37 |
| Std. Dev. | 0.7 | 0.6 | 0.3 | 0.8 | 0.6 |  |

EXAMPLE 7

Medical Device Surface Modification

Boston XO™ lenses were first cleaned with Boston Advance™ cleaning solution. Solutions of reactive polymers DMA-co-GMA [86/14] from Example 1 and DMA-co-MM-co-DMAPMA [67.7/10.6/21.6] from Example 4 were prepared as set forth below.

Treatment A was a 5 percent solution of DMA-co-GMA [86/14] (1.5 gm) and DMA-co-MAA-co-DMAPMA [67.7/10.6/21.6] (1.5 gm) dissolved in 60 ml of purified water. Lenses were then placed in the 5 ml of reactive polymer mixture and allowed to stand for 16 hours at room temperature and at 55° Celsius for one hour. The polymer solutions gelled under both sets of conditions. Lenses were removed from the gel and analyzed by XPS for surface composition.

Treatment B was a 2.5 percent solution of DMA-co-GMA [86/14] (0.75 gm) and DMA-co-MAA-co-DMAPMA [67.7/10.6/21.6] (0.75 gm) dissolved in 60 ml of purified water. Lenses were then placed in the 5 ml of reactive polymer mixture and allowed to stand for 16 hours at room temperature and at 55° Celsius for one hour. The polymer solutions gelled under both sets of conditions. Lenses were removed from the gel and analyzed by XPS for surface composition.

Treatment C was a 1 percent solution of DMA-co-GMA [86/14] (0.3 gm) and DMA-co-MM-co-DMAPMA [67.7/10.6/21.6] (0.3 gm) dissolved in 60 ml of purified water.-

Lenses were then placed in the 5 ml of reactive polymer-mixture and allowed to stand for 16 hours at room temperature and at 55° Celsius for one hour. The polymer solutions became viscous but did not gel under these conditions. Lenses were analyzed by XPS for surface composition.

TABLE 5

XPS Results from Example 7

| | C1s | N1s | O1s | F1s | Si2p | [F] Ratio |
|---|---|---|---|---|---|---|
| Controls | | | | | | |
| Average | 56.20 | 1.10 | 18.90 | 18.30 | 5.40 | 0.00 |
| Std. Dev. | 0.5 | 0.3 | 0.3 | 0.8 | 0.2 | |
| Treatment A at 55° C. for 1 hour | | | | | | |
| Average | 77.50 | 2.40 | 14.10 | 0.00 | 0.40 | 1.00 |
| Std. Dev. | 3.5 | 7.5 | 1.6 | 0.0 | 0.1 | |
| Treatment A at room temperature for 16 hours | | | | | | |
| Average | 70.10 | 3.70 | 23.80 | 0.00 | 0.30 | 1.00 |
| Std. Dev. | 1.4 | 0.2 | 0.7 | 0.0 | 0.4 | |
| Treatment B at 55° C. for 1 hour | | | | | | |
| Average | 75.28 | 9.73 | 14.82 | 0.11 | 0.06 | 0.99 |
| Std. Dev. | 0.5 | 0.4 | 0.1 | 0.2 | 0.1 | |
| Treatment B at room temperature for 16 hours | | | | | | |
| Average | 73.24 | 9.05 | 16.77 | 0.10 | 0.80 | 0.99 |
| Std. Dev. | 1.2 | 0.5 | 1.1 | 0.2 | 0.4 | |
| Treatment C at 55° C. for 1 hour | | | | | | |
| Average | 65.65 | 6.94 | 18.63 | 5.94 | 2.39 | 0.68 |
| Std. Dev. | 0.7 | 0.6 | 0.3 | 0.8 | 0.6 | |
| Treatment C at room temperature for 16 hours | | | | | | |
| Average | 64.30 | 6.14 | 20.30 | 5.35 | 3.12 | 0.71 |
| Std. Dev. | 1.6 | 1.0 | 24.0 | 1.0 | 0.9 | |

EXAMPLE 8

Medical Device Surface Modification with No Tertiary Amine

Boston XO™ lenses were first cleaned with Boston Advance™ cleaning solution. A solution of reactive polymers DMA-co-GMA [86/14] from Example 1 and DMA-co-MM [76/24] from Example 5 was prepared by combining 0.5 gm of each of the polymers above in 20 ml of purified water. Lenses were then placed in the 5 ml of reactive polymer mixture and allowed to stand overnight at room temperature. The treated lenses were then rinsed twice with purified water, padded dry with Kim Wipe™ tissues and submitted for XPS analysis the results of which are set forth below in Table 6. The nitrogen level increases were <2 percent while the fluorine and silicone levels drop only slightly when compared to Examples 6 and 7. The fluorine ratio was calculated as follows: $[F]_{control}-[F]_{test}/[F]_{control}$. The value represents the amount of fluorine covered by the coating polymer, where 1=100 percent coverage (0.08=8 percent of the fluorine covered).

TABLE 6

XPS Results from Example 8

| | C1s | N1s | O1s | F1s | Si2p | [F] Ratio |
|---|---|---|---|---|---|---|
| Controls | | | | | | |
| Average | 55.10 | 0.60 | 19.50 | 18.10 | 6.90 | 0.00 |
| Std. Dev. | 0.0 | 0.2 | 0.1 | 0.4 | 0.1 | |

TABLE 6-continued

XPS Results from Example 8

| | C1s | N1s | O1s | F1s | Si2p | [F] Ratio |
|---|---|---|---|---|---|---|
| Treatment at room temperature overnight | | | | | | |
| Average | 57.70 | 1.10 | 18.90 | 16.60 | 5.80 | 0.08 |
| Std. Dev. | 1.4 | 0.6 | 0.4 | 1.6 | 0.9 | |

Surface modified medical devices such as IOLs manufactured in accordance with the present invention can be of any design capable of being rolled or folded into a small cross section that can fit through a relatively small incision, i.e., 4.0 mm or less. For example, IOLs can be of a one-piece or multipiece design, and comprise optic and haptic portions. The optic portion is that portion which serves as the lens and the haptic portions are attached to the optic portion to hold the optic portion in proper alignment within an eye. The haptic portions may be integrally formed with the optic portion in a one-piece design or attached by staking, adhesives or other methods known to those skilled in the art in a multipiece design.

The subject IOLs may be manufactured to have the optic portion and the haptic portions made of the same or different materials. Preferably, in accordance with the present invention, the optic portion and the haptic portions are made of the same high-refractive index, low glass transition temperature composition. However, the optic portion and the haptic portions may also be manufactured from different compositions and/or different formulations of the same composition as described in detail in U.S. Pat. Nos. 5,217,491 and 5,326,506, each incorporated herein in their entirety by reference. Once the particular composition is selected, the material is either cast in molds of the desired shape or cast in the form of rods and lathed into disks. These disks are then machined at low temperatures below the glass transition temperature into IOLs. The IOLs whether molded or machined are then cleaned, polished, packaged and sterilized by customary methods known to those skilled in the art.

In addition to IOLs, the materials of the present invention are also suitable for use as other ophthalmic devices such as contact lenses, keratoprostheses, capsular bag extension rings, corneal inlays, corneal rings or like devices.

IOLs manufactured using the unique materials of the present invention are used as customary in the field of ophthalmology. In a surgical procedure, an incision is placed in the cornea of an eye, most commonly the natural lens of the eye is removed and the IOL manufactured and coated using materials of the present invention is inserted into the posterior chamber or lens capsule of the eye prior to closing the incision. However, the subject surface modified IOL implants are also suitable for implantation in an anterior chamber of an eye if so desired. Preferably implantation is accomplished using an implantation inserter, although other techniques known to those skilled in the art of ophthalmology are likewise acceptable.

While there is shown and described herein certain specific structures and compositions of the present invention, it will be manifest to those skilled in the art that various modifications may be made without departing from the spirit and scope of the underlying inventive concept and that the same is not limited to particular structures herein shown and described except insofar as indicated by the scope of the appended claims.

We claim:

1. A method of making a medical device comprising:
   providing a medical device with a surface comprising a polymeric material with first functional groups;

and; contacting the polymeric material with at least two hydrophilic copolymers, wherein one of the at least two hydrophilic copolymers comprises catalytic groups and second functional groups and one of the at least two hydrophilic copolymers comprises reactive groups that can react with the first functional groups of the polymeric material or the second functional groups of the other hydrophilic copolymer, the catalytic groups catalyzing a reaction between the first or the second functional groups and the reactive groups.

2. The method of claim 1 wherein said medical device is an intraocular lens or corneal inlay.

3. The method of claim 1 wherein said medical device is a contact lens.

4. The method of claim 1 the hydrophilic copolymer comprising the catalytic groups is prepared from a hydrophilic monomer selected from the group consisting of 3-(N,N-dimethylamino)propyl methacrylamide, 2-(N,N-dimethylamino)ethyl methacrylate, 2-(N,N-dimethylamino)ethyl acrylate, (N,N-dimethyl aminomethyl)styrene, N-[3-(N,N-dimethylamino)propyl]acrylamide and 3-(N,N-dimethylamino)propyl acrylate.

5. The method of claim 1 wherein said polymeric material is selected from the group consisting of 2-hydroxyethyl methacrylate, glyceryl methacrylate, 3-hydroxypropyl methacrylamide, methacrylic acid, acrylic acid, N-carboxy-β-alanine-N-vinyl ester, 2-isopropenyl-4,4-dimethyl-2-oxazolin-5-one, 2-vinyl-4,4-dimethyl-2-oxazolin-5-one, spiro-4'-(2'-isopropenyl-2'-oxazolin-5-one)cyclohexane, spiro-4'-(2'-vinyl-2'-oxazolin-5'-one)cyclohexane, 2-(1-propenyl)-4,4-dimethyl-oxazolin-5-one, methacrylic anhydride, acrylic anhydride, maleic anhydride and glycidyl methacrylate.

6. The method of claim 1 wherein said polymeric material is selected from the group consisting of silicone polymers, hydrocarbon and fluorocarbon polymers, hydrogels, acrylic polymers, polyesters, polyamides, polyurethanes, silicone polymers with hydrophilic monomer units, fluorine-containing polysiloxane elastomers and combinations thereof.

7. The method of claim 1 wherein said polymeric material is poly(HEMA-co-HOHEXMA).

8. The method of claim 1 wherein the hydrophilic copolymer comprising the catalytic groups is prepared from a hydrophilic monomer selected from the group consisting of N,N-dimethylacrylamide, N,N-dimethylmethacrylamide, N-methylmethacrylamide and N-methylacrylamide.

9. The method of claim 1 wherein the reactive groups present in one of the at least two hydrophilic copolymers are selected from the group consisting of epoxide functionality, carboxylic acid functionality, anhydride functionality, oxazolinone functionality and alcohol functionality.

10. The method of claim 1 wherein the reactive groups present in one of the at least two hydrophilic copolymers comprise epoxide functionality or oxazolinone functionality.

11. The method of claim 1 wherein the reactive groups present in one of the at least two hydrophilic copolymers includes N-vinylpyrrolidone.

12. The method of claim 1 wherein the first functional groups of the polymeric material and the second functional groups of the one of the at least two hydrophilic copolymer are carboxylic acid groups.

13. A method of making a medical device comprising:
providing a medical device with a surface comprising a polymeric material with first functional groups; and
contacting the surface of the polymeric material with at least two hydrophilic copolymers, wherein one of the hydrophilic copolymers is poly(DMA-co-GMA), and one of the hydrophilic copolymers comprises catalytic groups and second functional groups, the catalytic groups catalyzing a reaction between the first or the second functional groups and the poly(DMA-co-GMA).

14. The method of claim 13 wherein the reactive groups present in one of the at least two hydrophilic copolymers includes N-vinylpyrrolidone.

15. The method of claim 13 wherein the polymeric material is poly(HEMA-co-HOHEXMA).

* * * * *